Figure 1:
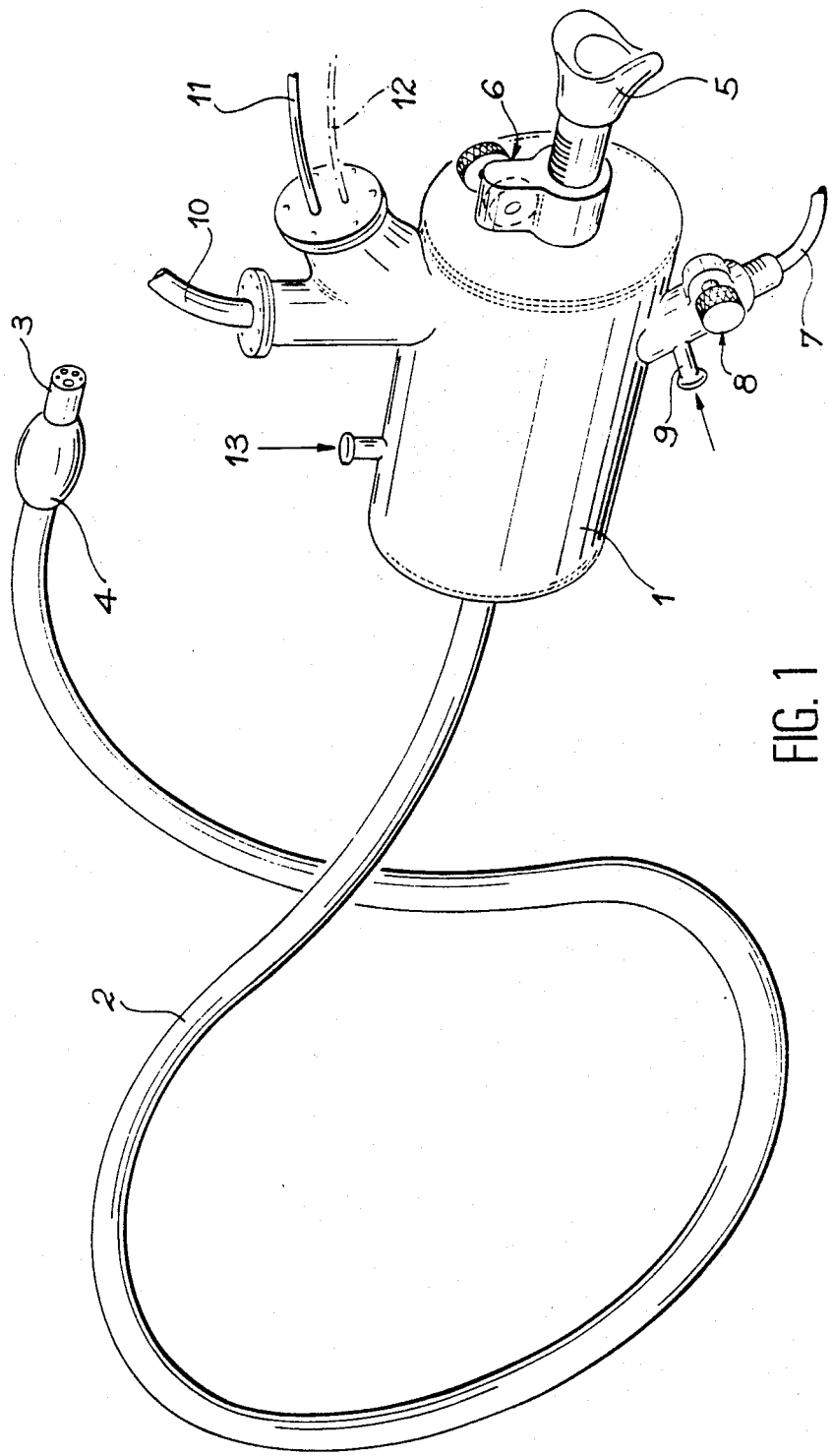

United States Patent [19]

Renaud

[11] Patent Number: 4,984,563
[45] Date of Patent: Jan. 15, 1991

[54] MULTIPLE FUNCTION OBSERVATION AND TREATMENT ENDOSCOPE AND PREPARATION PROCESS

[76] Inventor: Croisy Renaud, 15 Rue Marignac, Geneve/CH, France

[21] Appl. No.: 333,624
[22] PCT Filed: Jun. 27, 1988
[86] PCT No.: PCT/FR88/00340
    § 371 Date: Feb. 16, 1990
    § 102(e) Date: Feb. 16, 1990
[87] PCT Pub. No.: WO89/00023
    PCT Pub. Date: Jan. 12, 1989

[30] Foreign Application Priority Data

Jun. 29, 1987 [CH] Switzerland .................. 2453/87

[51] Int. Cl.⁵ .............................................. A61B 1/00
[52] U.S. Cl. .................................................... 128/6
[58] Field of Search .......................................... 128/6

[56] References Cited

U.S. PATENT DOCUMENTS

| | | | |
|---|---|---|---|
| 2,888,017 | 5/1959 | Wallace | 128/7 X |
| 4,146,019 | 3/1979 | Bass et al. | 128/6 |
| 4,171,943 | 10/1979 | Tschanz et al. | 425/392 |
| 4,313,431 | 2/1982 | Frank | 128/7 |
| 4,561,446 | 12/1985 | Hetz | 128/7 X |
| 4,737,142 | 4/1988 | Heckele | 128/6 X |
| 4,899,732 | 2/1990 | Cohen | 128/6 |

FOREIGN PATENT DOCUMENTS

| | | |
|---|---|---|
| 0066185 | 12/1982 | European Pat. Off. . |
| 0112148 | 6/1984 | European Pat. Off. . |
| 0188273 | 7/1986 | European Pat. Off. . |
| 0195375 | 9/1986 | European Pat. Off. . |
| 2385372 | 10/1978 | France . |
| 2167668 | 6/1986 | United Kingdom . |

Primary Examiner—William H. Grieb
Attorney, Agent, or Firm—Oblon, Spivak, McClelland, Maier & Neustadt

[57] ABSTRACT

This preparation process for an observation and treatment endoscope for introduction into the human body through an inner duct of a synthetic material cylindrical tube (2) serving as a catheter extending between an external control and observation head (1) and an internal intervention end (3) and having a certain number of cylindrical longitudinal hollow ducts (17, 22, 23) for receiving the illuminating means (21), the observation means (14) and the treatment means (7) is characterized in that it comprises moulding the tube (2) by placing synthetic material in the pasty state around longitudinal mandrels, whose positions and diameters correspond to the future hollow ducts of the tube and ultrafine optical illuminating fibres, solidifying the synthetic material and then extracting the different mandrels.

4 Claims, 3 Drawing Sheets

MULTIPLE FUNCTION OBSERVATION AND TREATMENT ENDOSCOPE AND PREPARATION PROCESS

DESCRIPTION

The invention relates in general terms to the medical observation and treatment of the human body with the aid of endoscopes, which are introduced through a natural or artifical internal duct.

Probes or endoscopes are already known making is possible to carry out observations and/or certain treatments in given areas of a cavity of the human body. Such probes are currently used e.g. in urology and gastroenterology. In their most general present form, the mainly have in a cylindrical plastic or synthetic material tube serving as a catheter and extending between an externally controlled observation head manipulated by the surgeon and an internal intervention or operation end, a certain number of longitudinal hollow ducts for receiving illuminating means, observation means and treatment means.

The appearance a few years ago of optical fibres has led to significant improvements to such equpment by permitting the easy illumination and observation of the working area. In addition, laser probes constituted by an optical fibre transmitting the radiation of a power laser and widely used for obtaining, as a function of the wavelength of the laser light, either a local burning of the undesired body part, or the crushing of a renal calculus. An endoscopic operating probe of this type is e.g. described in GB-A-2 167 688, published on Jun. 4th 1986. This document shows an endoscope having an externally controlled observation head and an operating end connected to one another by a plastic tube having four orifices 3, 7, 8 and 10 and used for the observation, illumination, passage of an operating instrument and circulation of an irrigating liquid for the working area. This probe is completed at its operating or intervention end by a balloon 12, which can be inflated from the outer control head and which permits, following the introduction of the probe into the internal duct of the human body, to ensure a relative fixing thereof by gripping along the walls of said duct.

This document, which summarizes the state of the art prior to the present application, also provides an understanding and illustration of the disadvantages of such equipment and reference will be briefly made thereto hereinafter.

Firstly, an endoscopic probe according to GB-A-2 167 688 is not functionally viable in the state in which it is described in said document for the following reason. When, as is often the case, the operating instrument introduced through the duct 8 is a fibre supplied by power laser, e.g. of the YAG type or a dye laser, the distal end of said fibre is significantly heated during its operation. This phenomenon is increased and makes the operating instrument inoperable when organic deposits agglutinate at the end of the laser fibre, which reaches temperatures from 100° C. (boiling point of the water of the cells) to more than 1000° C. Unless special precautions are taken, the thus enitted thermal energy may destroy the entire internal operating end of the tube and in particular that of the illuminating and observation fibres (the latter being destroyed as from 70° C.) and also the lens by the thermal shock action.

Moreover, an apparatus according to said document and whose tube is produced by extrusion means that the latter will have minimum diameter values of approximately 4 mm, without it being possible to drop below this size. This limits the use of such endoscopes, particularly with regards to the examination of small ducts in the human body such as arteries (coronary arteries in cardiology), veins or the introduction of a probe for crushing renal calculi, whereby in this case the probe necessarily must clear the uterovesical orifice located at the outlet from the bladder and whose normal opening in the adult is approximately 2.3 mm. Therefore, for the treatment of renal calculi using the prior art probes and instruments like that described in the aforementioned British document, the surgeon has to bring about a progressive expansion of the opening, which requires a general anasthesia lasting several hours.

Finally, all the hitherto know endoscopes are monofunctional, i.e. they are all designed in the case of operating equipment, to operate with a single given probe, e.g. a laser probe, an ultrasonic probe or gripping tweezers. Thus, if when operating a surgeon successively has to use several operating methods, in theory it is necessary for him to change the endoscope on each occasion, which can not be carried out in practice.

The object of the present invention is to provide an endoscopic observation and treatment apparatus making it possible to obviate the disadvantages referred to hereinbefore by offering equipment which is significantly miniaturized compared with the known equipment and making it possible, with the same apparatus, to realize several different functions during an operation, as required by the surgeon.

The present invention therefore relates to a preparation process for an endoscopic observation and treatment apparatus for introduction into the human body through an internal duct of a cylindrical synthetic material tube serving as a catheter extending between an externally controlled observation head and an internal operating end and having a certain number of cylindrical, longitudinal, hollow ducts for receiving the illuminating means, the observation means and the treatment means, characterized in that it consists of moulding the tube by bringing the synthetic material in the pasty state around longitudinal mandrels, whose positions and diameters correspond to the future hollow ducts of said tube and ultrafine illuminating optical fibres, solidifying the synthetic material and then extracting the different mandrels.

This process for the preparation of the cylindrical, bicompatible synthetic material tube (PVC, Teflon, etc.) serving as a catheter and which consists of producing the same by moulding around previously positioned mandrels leads to certain of the essential advantages of the invention. Thus, it firstly and particulary makes it possible to reduce to very small sizes below 0.15 mm and even down to 0.05 mm, the thickness of the walls separating the longitudinal hollow ducts of the tube. This leads to a considerable space saving compared with the plastic material tubes obtained by the method used up to now, namely extrusion, which does not make it possible to obtain good quality hollow ducts separated by walls of size below 0.20 mm. The above figures immediately reveal the interest of the production process by moulding the tubes from synthetic material, because the significance of the miniaturization of the endoscopic probe for the patient and surgeon and obvious.

Moreover, there are now ultrafine optical fibres with a diameter close to 50 micrometers, which makes it possible by moulding directly during production a large number of said ultrafine fibres in the free spaces between hollow ducts to obtain the same cross-section of transmission for the lighting flux with a distribution, whose overall dimensions in the sense of the diameter of the tube and much smaller, whilst leading to a better catheter flexibility. This is the second advantage of using moulding, because in the case of production by extrusion, it would be impossible to obtain channels of 50 micrometers and to then introduce into them one by one the different illuminating optical fibres.

The invention also relates to a multifunction observation and treatment endoscopic apparatus for introduction into the human body through a natural or artificial internal duct, which mainly comprises a cylindrical synthetic material tube serving as a catheter and extending between an externally controlled observation head and an internal intervention or operating end provided with an inflatable fixing balloon, a certain number of cylindrical longitudinal hollow ducts for receiving illuminating means, observation means and treatment means, characterized in that the tube is obtained by moulding with an external diameter below 2 mm and in that the hollow duct are separated from one another by walls which, at the location of their minimum thickness, have a size below 0.10 mm and which, if need be, can descend to 0.05 mm, said tube having illuminating means constituted by a plurality of ultrafine optical fibres with an individual diameter of approximately 50 $\mu$m distributed and embedded in the synthetic material of the tube during the preceding moulding operation, an observation optical fibre, whose intervention or operation side end is provided with optical accomodation means and whereof the observation side end is provided with a screw and rack system permitting the axial displacement of the fibre within the tube, an intervention or operation fibre, which is also regulatable in axial translation within the tube with the aid of a screw and rack system fixed to the observation head, an adequate radial clearance being provided between the tube and the said fibre to permit the circulation of a cooling liquid along the same and a hollow channel with a diameter close to 1 mm for the circulation of an irrigation and/or suction liquid and the introduction, as a function of the instantaneous needs of the surgeon, of a random operating means, particularly and optionally, one of the operating means chosen from among ultransonic probes, microdrills, biopsy probes, coagulation probes, spark probes, laser probes and optical fibre pressure measuring probes.

Among the original features of the aforementioned apparatus are the general dimensions of the tube obtained by moulding with an external diameter below 2 mm, as well as the illuminating means constituted by a plurality of ultrafine optical fibres embedded in the synthetic material of the tube during manufacture. These two characteristics have an essential effect on the miniaturization and make it possible to substantially divide by two the present diameter of endoscopic probes.

Moreover and still in accordance with the present invention, the observation optical fibre and the intervention fibre are both regulatable in translation by means of a screw and rack system permitting their displacement with respect to the observation head. This very interesting feature of the apparatus according to the invention makes it possible to create acceptable working conditions at the internal intervention or operation end of the catheter for reasons:

(a) The reciprocal displacement in translation of the optical observation fibre and the invention fibre makes it possible, by reciprocal axial displacement, to avoid burning the observation fibre and the complete catheter intervention end when, as was mentioned hereinbefore, the intervention fibre is a laser fibre, whose end can reach temperatures of 1200° C.

(b) This structure, which permits the axial displacement of the optical fibre, permits the movement of the latter alone by a few centimeters in front of the intervention end either to clear an unexpected obstacle occuring on introducing the catheter, or for carrying out the calibration of a contraction zone.

According to the invention, the intervention fibre can either be a laser fibre, or an ultrasonic fibre. As a function of the wavelength which is transmitted by them, laser fibres can be used either for buring an undesirable tissue or, particularly in urology or in gastroenterology, for crushing a calculus by thermal shock. The miniaturization achieved with the aid of the means according to the invention and which leads to a tube with an external diameter below 2 mm makes it possible, particularly in urology, to achieve a very substantial advance because the thus obtained instrument clears, without any need for expansion and consequently general anesthesia, the uterovesical passage making it possible to reach the kidney after clearing the bladder.

Finally, the presence in the synthetic material tube of a hollow channel with a diameter close to 1 mm and reserved for the circulation of the a suction and/or irrigation liquid and with a size adequate for simultaneously permitting the introduction of a random operating means as a function of the instantaneous needs of the surgeon gives the apparatus its multifuctional character. Thus, according to the invention, it is possible to use said channel either for a second laser fibre, which in this case would have a different function from the first intervention fibre, or for an ultrasonic probe, so that the apparatus according to the invention makes it possible to use either two laser intervention fibres, or two ultrasonic intervention fibres, or in combination a laser fibre and an ultrasonic fibre, whereby the latter can also be replaced in situ and during the operation by a microdrill, by a biospy probe, a coagulation probe, a spark probe, etc. In the case of using a single ultrasonic probe, the latter can be used as a bistoury for its destruction function. In this case where the apparatus according to the invention is used for the simultaneous introduction of two ultrasonic probes, it is e.g. possible to use one as the emitting probe and the other as the receiving probe, which makes it possible to carry out a local echrography and even, when there is a blood flow in a blood vessel, echography by Doppler effect. Such ultrasonic probes and microdrills can be of particular interest in cardiology, where their introduction either into coronaries having stenoses, or into cardiac cavities, makes it possible to obtain vital information on (or to treat) the state of the wall of the vessel or inner cavities of the heart. Doppler effect echography can also make it possible to study in situ the movement of the heart valves.

Spark probes can be used for crushing calculi or mineral concretions. Biopsy probes are also clearly of interest. Optical fibre pressure measuring probes can be very useful in traumatological neurosurgery, e.g. for directly observing the pressure within an intracranial fossa filled with cerebrospinal fluid. In an operation of this type, the inventive apparatus is directly introduced into the skull with the aid of an orifice made therein. All the above examples illustrate the multifunctional character of the apparatus according to the invention which makes it possible, with the aid of a single endoscope introduced into a duct of the body, to carry out a sequence of successive operations or interventions of different types.

The invention will be better understood through referring to the following exemplified description of the endoscope, which is given in an illustrative and non-limitative manner with reference to FIGS. 1 to 4, wherein show:

FIG. 1 An overall view of the apparatus according to the invention.

Figure 2:
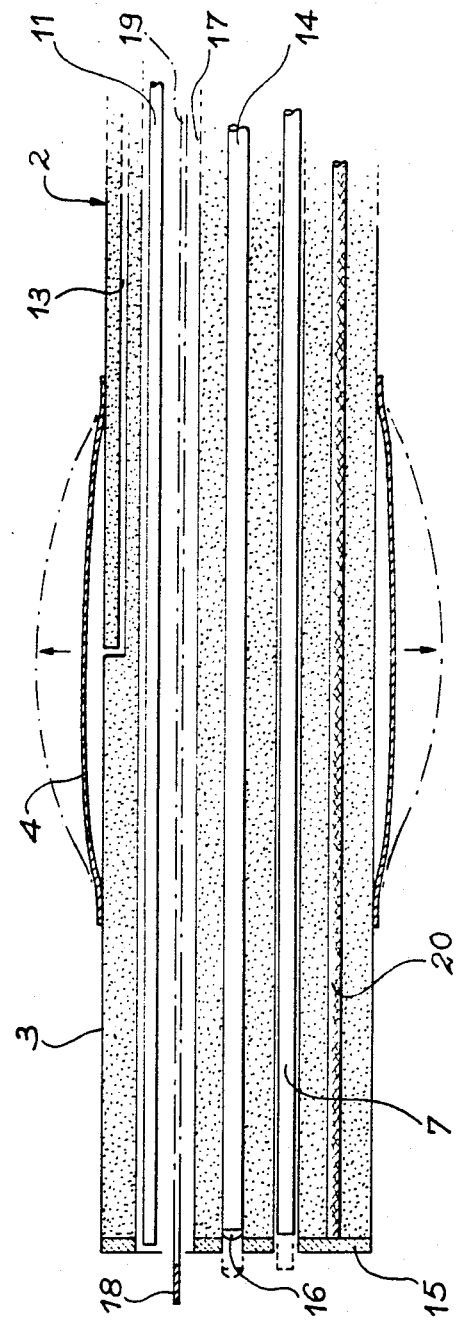

FIG. 2 a turned down sectional view of the operating end of the apparatus.

Figure 3:
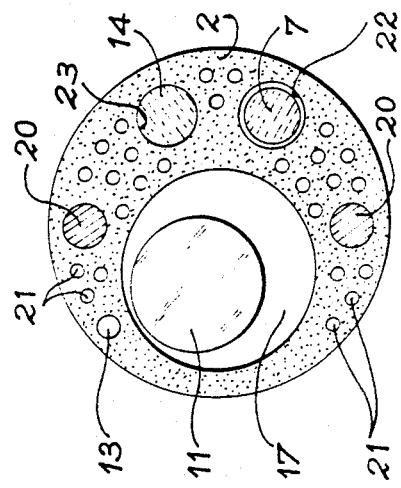

FIG. 3 A section along the tube of FIG. 2, where the respective dimensions of the different ducts and probes have been respected.

Figure 4:
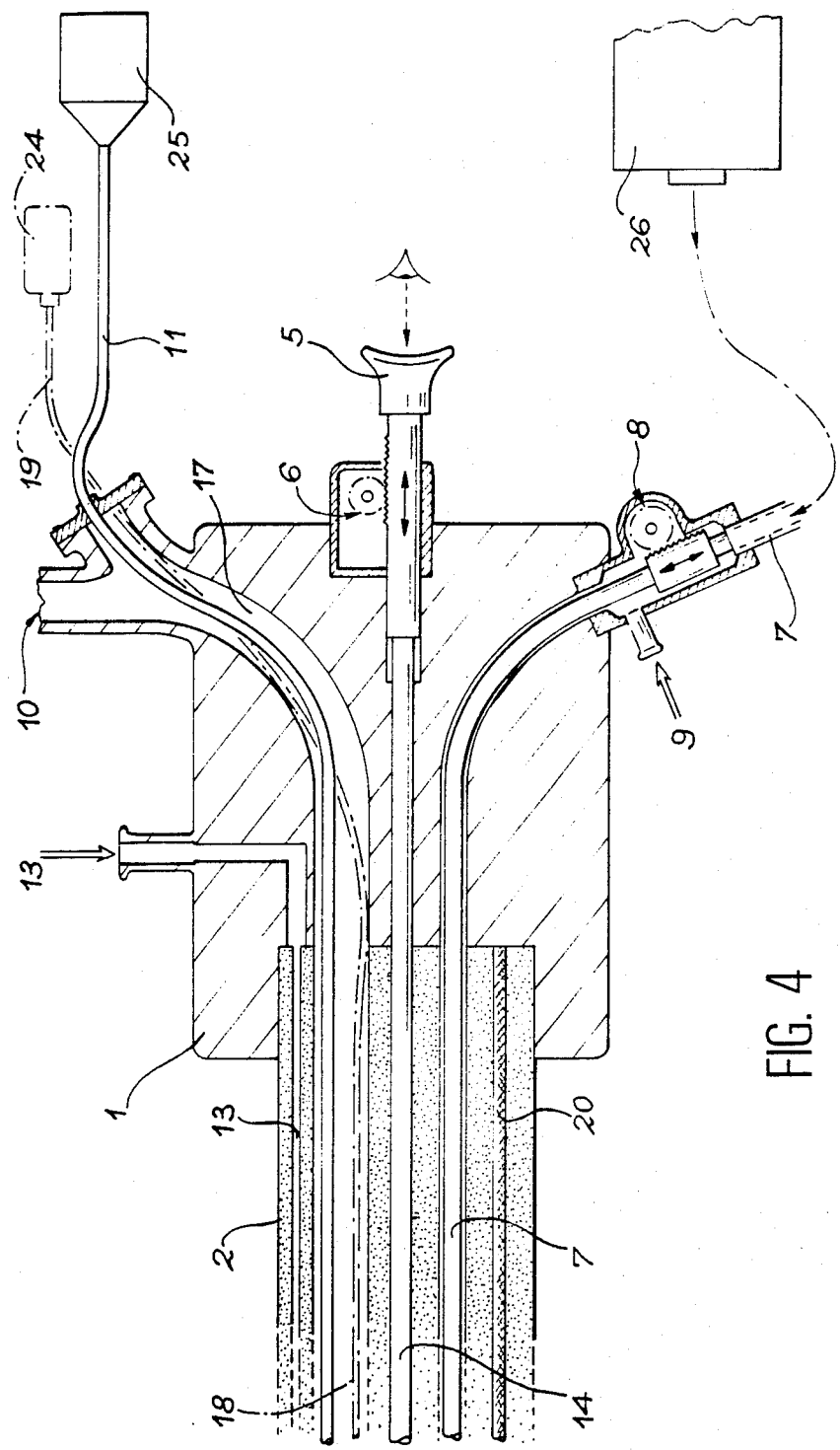

FIG. 4 A sectional view of the external control and observation head of the endoscope.

FIG. 1 shows the multifunction treatment and observation endoscope according to the invention and it is possible to see three essential elements, namely the externally controlled observation head 1, the synthetic material tube 2 for transmitting light information and for the introduction of operating instruments, as well as the internal intervention or operation end 3, provided with its inflatable fixing balloon 4.

To the observation head 1 are fixed an ocular device 5 corresponding, as will be shown hereinafter, with the observation fibre, a screw and rack device 6 making it possible to regulate, within the tube 2, the axial translation state of said observation fibre.

In the example of FIG. 1, the first intervention fibre is a laser fibre 7 regulatable in translation in tube 2 with the aid of the screw and rack device 8. According to the invention, a radial clearance is left between the laser fibre 7 and the duct which it occupies within tube 2, in order to allow the circulation of a cooling fluid which penetrates the system at 9.

According to the invention, the observation and control head 1 also has the pipe 10 for the introduction and reception of the irrigation and/or suction liquid flow and, in the same hollow internal duct, the channels for introducing an ultrasonic probe 11 or a random operating instrument 12 chosen from among those referred to hereinbefore. Finally, said external control and observation head 1 also has an orifice 13 into which can be introduced the inflating air for balloon 4, when with the endoscopic probe having reached the desired location within the human body, the surgeon decides to fix its translation state with respect to the wall of the introduction duct by inflating balloon 4.

In FIG. 2, which is a turned down section level with the operating end 3 of duct 2, it is possible to see the observation fibre 14, the laser fibre 7 and the ultrasonic probe 11 in their respective longitudinal hollow ducts. For reasons of greater clarity in said FIG. 2 the respective dimensions of the different components have not been respected. The synthetic material tube 2 is terminated at its inner intervention or operating end 3 by a thermal coating 15 for providing protection against heating occurring at this point through the laser fibre 7. The end of the observation fibre 14 is also provided with an accommodation lens 16 connected to said end of the fibre 14, or more simply constituted by the appropriate size of said fibre end. According to the invention, the hollow duct 17 serving both for the irrigation and introduction of the ultrasonic probe 11 can also be used for supplying to the operating point another random treatment means, e.g. in the case of FIG. 2, a microdrill 18 mounted on the end of a cable 19, which can be manipulated from the external control head.

Finally, in order to make the apparatus completely opertional, tube 2 has in appropriate hollow ducts at least one flexible rigidification core 20 for giving the probe a desirable profile during its introduction and its advance in the inner duct of the human body. An inflatable balloon 4 is also provided at the end 3 of tube 2. The balloon is inflatable in per se known manner with the aid of a pressurized air flow introduced in duct 13. In FIG. 2 the walls of said balloon are shown in continuous line form in its inoperative position and in mixed line form in its inflated position, where to a certain extent it permits the fixing of the tube in translation along the not shown wall of the internal duct into which it is introduced.

As has been explained hereinbefore, the translation regulating means 6 and 8 of the observation fibre 14 and the laser fibre 7, as well as the thermal coating 15 make it possible, by choosing the translation state of fibres 7 and 14, to protect against heating by the laser the end 16 of the observation fibre 14.

FIG. 3 is a section along tube 2 of FIG. 2 and gives a more precise idea of the reciprocal dimensions of the three hollow ducts traversing said tube, as well as the ultrafine optical fibres 21 carrying the light for illuminating the treated area.

In FIG. 3, it is once again possible to see the tube 2 and the rigidification cores 20. It is also possible to see the various ultrafine optical fibres 21 embedded in the synthetic material mass of tube 2 in the areas left free by the three ducts 17, 22 and 23. As explained in the introduction to the text, an essential feature of the invention is the process for producing said tube 2 and the ducts 17, 22, 23 traversing it, which is carried out by moulding using mandrels which are subsequently extracted. In accordance with the production process for said tube 2, the different ultrafine optical fibres 21, whose diameter is close to 50 micrometers, are integrated into the synthetic material mass 2 and embedded in the latter at the time of moulding synthetic material 2. Channel 22 for receiving the laser fibre 7 has a diameter of approximately 0.3 mm, as has the channel 23 for receiving the observation fibre 14. However, an annular space is provided between the laser fibre 7 and the channel 22 for permitting the circulation of the cooling fluid injected by orifice 9, cf. FIG. 1. Channel 17 for the introduction of ultrasonic probe 11 and microdrill 18 has a diameter of approximately 1 mm which is adequate to at the same time permit the circulation of the irrigation liquid for the working area. The external dimensions of the tube 2 of FIG. 3 are, in the present embodiment, a diameter of 2 mm.

The intensity of the illuminating light flux carried by the different ultrafine fibres 21 is directly dependent on the surface of the cross-sections of these different fibres and through having distributed large numbers thereof by embedding them in the synthetic material mass of the tube 2 makes it possible to obtain an equal lighting for reduced overall dimensions consisting of that of a single circular fibre with a surface equal to the sum of the elementary surfaces of the fibres 21. Moreover, the distribution of these illuminating fibres 21 in a large number of ultrafine fibres leads to greater strength and bending resistance on the part of the illuminating device compared with the solution having a single fibre.

FIG. 4 shows in section the external control and observation head 1 and its junction with the synthetic material tube 2. It is possible to see the various elements already described with their relevant reference numerals, as well as additionally the control motor 24 for the microdrill 18 using the metal cable 19, the ultrasonic source 25 supplying fibre 11 with ultrasonic operating power and the laser 26 supplying luminous energy to laser fibre 7. FIG. 4 also shows in greater detail the arrangement of the screw and rack system 8 and the system 9 for introducing the cooling liquid making it possible to inject a certain quantity thereof between fibre 7 and the hollow duct corresponding to the interior of the synthetic material tube 2.

What is claimed is:

1. Multifunction observation and treatment endoscopic apparatus for introduction into the human body through a natural or artifical internal duct, which comprises:

a cylindrical synthetic material tube serving as a catheter and extending between an externally controlled observation head and an internal end provided with an inflatable fixing balloon, said tube including a plurality of cylindrical longitudinal hollow duct for respectively receiving illuminating means, observation means and treatment means, wherein the tube has an external diameter of less than 2 mm and wherein the hollow ducts are separated from one another by walls which, at the location of their minimum thickness, have a size of less than 0.10 mm, said illuminating means including a plurality of ultrafine optical fibres with an individual diameter of approximately 50 $\mu$m distributed and embedded in the tube, said observation means including an optical fibre, having an end provided with optical accommodation means and having an observation side end which includes a screw and rack system for permitting axial displacement of the fibre within the tube, a fibre which is regulatable in axial translation within the tube; a screw and rack system fixed to the observation head for regulating said fibre in axial translation within the tube wherein a radial clearance is provided between the tube and said fibre to permit the circulation of a cooling liquid along the same and a hollow channel with a diameter of substantially 1 mm for the circulation of a liquid and the introduction, as a function of instantaneous needs of the surgeon, of random operating means.

2. Endoscopic apparatus according to claim 2, wherein the fibre which is regulatable comprises a laser radiation transmission fibre.

3. Endoscopic apparatus according to claim 2, wherein the fibre which is regulatable comprises an ultransonic power transmission fibre.

4. Endoscopic apparatus according to claim 2 wherein the end of the tube includes thermal protection means.

* * * * *